United States Patent [19]

Ishino et al.

[11] Patent Number: 5,237,107

[45] Date of Patent: Aug. 17, 1993

[54] MAGNESIUM, ALUMINIUM COMPLEX COMPOUNDS, PROCESS FOR PREPARING THE SAME AND PROCESS OF ALDOL CONDENSATION DEHYDRATION PRODUCTS USING THE SAME

[75] Inventors: Masaru Ishino, Chiba; Masami Fukao, Shiga; Kazuaki Sasaki, Osaka; Gohfu Suzukamo, Osaka; Masao Sasaki, Osaka, all of Japan

[73] Assignee: Sumitomo Chemical Company, Limited, Osaka, Japan

[21] Appl. No.: 879,583

[22] Filed: May 7, 1992

[30] Foreign Application Priority Data

May 10, 1991 [JP] Japan .................................. 3-105928

[51] Int. Cl.$^5$ .......................................... C07C 45/00
[52] U.S. Cl. .................................... 568/463; 568/464
[58] Field of Search ............................... 568/463, 464

[56] References Cited

U.S. PATENT DOCUMENTS

| | | |
|---|---|---|
| 2,403,876 | 7/1946 | Nord .................................. 568/463 |
| 4,086,188 | 4/1978 | Reichle .............................. 568/463 |
| 4,165,339 | 8/1979 | Reichle .............................. 568/463 |
| 4,458,026 | 7/1984 | Reichle .............................. 568/463 |
| 4,476,324 | 10/1984 | Reichle ............................. 568/388 |
| 5,144,089 | 1/1992 | Arena et al. ....................... 568/463 |

FOREIGN PATENT DOCUMENTS

| | | |
|---|---|---|
| 0146927 | 7/1985 | European Pat. Off. ............ 568/388 |
| WO9012645 | 11/1990 | PCT Int'l Appl. . |
| WO9113831 | 9/1991 | PCT Int'l Appl. . |

OTHER PUBLICATIONS

Applied Catalysis, 48 (1989) 63-70 "Addition of metal cations to magnesium oxide catalyst for the aldol condensation of acetone", Tanabe, K. et al pp. 63-69.
Chemical Abstracts, vol 107, No. 5, Aug. 1987, p. 644.
Chemical Abstracts, vol. 98, No. 22, 1983, p. 140.
Chemical Abstracts, vol. 85, 1976, p. 138.
Chemical Abstracts, vol. 102, No. 22, Jul. 1985, p. 134.

Primary Examiner—Werren B. Lone
Attorney, Agent, or Firm—Cushman, Darby & Cushman

[57] ABSTRACT

Magnesium.aluminium complex compound useful for aldol condensation dehydration is prepared by allowing a solution of magnesium salts and a solution of aluminium salts to react with ammonia and then heating the thus obtained precipitate at a temperature of 400°–700° C.

12 Claims, No Drawings

MAGNESIUM, ALUMINIUM COMPLEX COMPOUNDS, PROCESS FOR PREPARING THE SAME AND PROCESS OF ALDOL CONDENSATION DEHYDRATION PRODUCTS USING THE SAME

The present invention relates to magnesium aluminium complex compounds, a process for preparing the same and a process of aldol condensation dehydration products using the same.

Magnesium.aluminium complex compounds are well known as a catalyst for condensation dehydration of such carbonyl compounds as ketones and aldehydes to produce aldol condensation dehydration products, i.e., a catalyst for aldol condensation dehydration.

The magnesium.aluminium complex compounds are prepared by allowing sodium hydroxide to react with a solution of magnesium salts and aluminium salts to prepare a precipitate, doping the precipitate with lithium or zinc salts and heating the product at a temperature not higher than about 400° C. (U.S. Pat. No. 4,535,187); or adding magnesium salts and aluminium salts to a solution of sodium hydroxide and sodium carbonate to produce a precipitate, and heating the precipitate at a temperature within the range of 300° to 600° C. (U.S. Pat. No. 4,476,324). However, magnesium.aluminium complex compounds obtained are not satisfactory in respect to catalytic activity and selectivity. In addition, there is a difficulty in the former process that lithium or zinc salts have to be used as a starting material and such a complicate operation as doping is needed. The latter process needs two alkalis such as sodium hydroxide and sodium carbonate for production of precipitate.

After the present inventors studied to dissolve such problems as mentioned above, they found that magnesium.aluminium complex compounds having large catalytic activity are obtained with ease when specific alkali or ammonia is used in the step for production of precipitate. The present invention is made on the basis of this finding.

According to the present invention, magnesium.aluminium complex compounds is provided by allowing a solution of magnesium salts and a solution of aluminium salts to react with ammonia to produce a precipitate, and heating the precipitate at a temperature within the range of 400° to 700° C. The present invention further provides greatly active aldol condensation dehydration catalysts containing the magnesium.aluminium complex compounds above mentioned. The present invention further provides an economical process for preparing magnesium.aluminium complex compounds by allowing a solution of magnesium salts and a solution of aluminium salts to react with ammonia to produce a precipitate, and heating the precipitate at a temperature within the range of 400° to 700° C. In condensation dehydration of carbonyl compounds to prepare aldol condensation dehydration products, the present invention further provides an economical process for preparing aldols in the presence of a catalyst prepared by allowing solutions of magnesium salts and aluminium salts to react with ammonia to prepare a precipitate and heating the precipitate at a temperature within the range of 400° to 700° C.

The present invention is explained in detail.

Magnesium salts are water soluble ones such as magnesium nitrate and magnesium acetate. Aluminium salts are water soluble ones such as aluminium nitrate and aluminium lactate. Ratio of magnesium salts to aluminium salts is 10:1 to 1:5 by atom, preferably 3:1 to 1:1.

A solution of magnesium salts and a solution of aluminium salts are allowed to react with ammonia to prepare a precipitate. The ammonia is usually in the form of an aqueous solution. An amount of ammonia is usually within the range of 0.5 to 2 times, preferably not more than one time, as much as theoretical equivalents of magnesium salts and aluminium salts.

The reaction with ammonia is carried out by adding an ammonia solution to a mixed solution of the salts. Alternatively, the mixed solution of salts is added to the ammonia solution. Alternatively, the three solutions are mixed together at the same time. Gaseous ammonia may be introduced in the mixed solution of salts.

A precipitate is separated by filtration or the like. The precipitate is usually washed and dried before being calcined at a temperature within the range of about 400° to 700° C. If the temperature is not higher than about 400° C. or higher than about 700° C., activity of the product is degraded. Calcining varies depending on temperature but usually is within the range of 0.1 to 10 hours.

Magnesium.aluminium complex compounds thus obtained are useful for aldol condensation dehydration. The compounds may be carried on carriers or diluted with diluents. Alternatively, binders or the like may be mixed therewith in order to improve mechanical strength.

The aldol condensation dehydration is carried out batchwisely or continuously. The catalysts may be used in a fixed bed or a fluidized bed system.

Materials for aldol condensation dehydration are carbonyl compounds including ketones such as acetone, methyl ethyl ketone, methyl isobutyl ketone, diethyl ketone, cyclopentanone and cyclohexanone and aldehydes such as acetaldehyde and butyl aldehyde.

The aldol condensation dehydration reaction is conducted in a known manner. For instance, a production of mesityl oxide and isophorone is effected at a temperature within the range of 250° to 400° C., preferably 270° to 330° C. under a pressure within the range of atmospheric pressure to 5 Kg/cm$^2$. Feeding speed of materials is usually within the range of 0.1 to 10 h$^{-1}$ in LHSV (liquid hourly space velocity), preferably in the range of 1 to 5 h$^{-1}$.

The present magnesium.aluminium complex compounds have high aldol condensation dehydration catalytic activity to effect condensation dehydration with efficiency.

One of advantages is that the use of only one alkali or ammonia is able to produce magnesium.aluminium complex compounds having high catalytic activity.

The present invention is explained by the following examples but is not restricted thereto.

EXAMPLE 1-1

In a flask (3) containing deionized water (640 g) under a nitrogen atmosphere were charged magnesium nitrate [Mg(NO$_3$)$_2$.6H$_2$O, 153.6 g] and aluminium nitrate [Al(NO$_3$)$_3$.9H$_2$O, 150 g]. The solution was added drop by drop to a solution of 28% ammonia water (300.4 g) and deionized water (800 g).

After the addition was over, the solution was stirred for 3 hours and filtered. To wet cake was added deionized water (1600 g) before being washed and filtered. This step was repeated three times. The cake was dried at 100° C. under reduced pressure and then calcined at a temperature of 550° C. for 2 hours, to obtain white solids (43.4 g).

EXAMPLE 1-2

A stainless tube (16 mm $\phi \times 250$ mm) charged with the catalyst of example 1 (24-48 mesh after shaped, 10 ml, 6.53 g) was kept at 2.8 kg/cm$^2$ (guage), while nitrogen gas (20 ml/min) was fed. After the temperature of the tube was raised to 300° C., acetone (10 ml/H) was charged. After 18 hours were elapsed, a solution flowed out was taken out. Gas chromatography assay was effected. Then, acetone-feeding rate was changed within the range of 10 to 40 ml/H, and product assay was made. The results are shown in Table 1. Recovery rate of reaction solution against acetone was 98-99%.

TABLE 1

| Flow rate of acetone (ml/H) | Solution composition | | |
|---|---|---|---|
| | Acetone (wt %) | Mesityl oxide (wt %) | Isophorone (wt %) |
| 10 | 46.8 | 1.5 | 22.5 |
| 30 | 61.0 | 2.5 | 20.0 |
| 40 | 69.0 | 2.9 | 17.3 |

Notes:
Mesityl oxide:
4-methyl-3-pentene-2-one + 4-methyl-4-pentene-2-one
Isophorone:
3.3.5-trimethyl-2-cyclohexene-1-one + 3.3.5-trimethyl-3-cyclohexene-1-one

COMPARATIVE EXAMPLE 1-1

To a flask (3 l) charged with deionized water (800 g) under a nitrogen atmosphere at a temperature of 15°-20° C. were fed 50% sodium hydroxide (192 g) and sodium carbonate (40 g). To the solution were added drop by drop over 30 minutes a solution of magnesium nitrate Mg(NO$_3$)$_2$.6H$_2$O, 153.6 g) and aluminium nitrate Al(NO$_3$)$_3$.9H$_2$O, 150 g) in deionized water (640 g). After the solution was stirred at a temperature in the range of 15° to 20° C. for a period of 30 min., the temperature was raised to 65° C. and stirring was made for 18 hours at the same temperature. After the solution was cooled to room temperature, filtration, washing and drying under reduced pressure were effected in the same manner as in Example 1-1. Calcing at 450° C. for 18 hours gave white solids (35.2 g).

COMPARATIVE EXAMPLE 1-2

A reaction was carried out in the same manner as in Example 1-2 in the presence of the catalyst above (24-48 mesh after shaped, 10 ml, 4.12 g). The results are shown in Table 2. Recovery rate of reaction solution was 98-99%.

TABLE 2

| Flow rate of acetone (ml/H) | Solution composition | | |
|---|---|---|---|
| | Acetone (wt %) | Mesityl oxide (wt %) | Isophorone (wt %) |
| 13.6 | 74.4 | 3.9 | 11.6 |
| 19.9 | 76.5 | 4.1 | 10.5 |
| 25.0 | 79.7 | 4.4 | 8.9 |

EXAMPLES 2-1 AND 3-1 AND COMPARATIVE EXAMPLE 2-1

Example 1s were repeated except that magnesium salts and aluminium salts were changed as shown hereinafter to obtain white solids.

TABLE 3

| Examples | Magnesium salts (g) | | Aluminium salts (g) | |
|---|---|---|---|---|
| Ex. 2-1 | Mg(NO$_3$)$_2$.6H$_2$O | 123.2 | Al(NO$_3$)$_3$.9H$_2$O | 180.1 |
| Ex. 3-1 | Mg(NO$_3$)$_2$.6H$_2$O | 263.3 | Al(NO$_3$)$_3$.9H$_2$O | 42.8 |
| Comp. 2-1 | MgSO$_4$.7H$_2$O | 147.9 | Al$_2$(SO$_4$)$_3$.18H$_2$O | 133.3 |

EXAMPLES 2-2 AND 3-2 AND COMPARATIVE EXAMPLE 2-2

Example 1-2s were repeated except that catalysts obtained above were replaced by those obtained above. The results are shown in Table 4. Recovery rates of reaction solutions were 98-99%.

TABLE 4

| Examples | Catalysts | Flow rate of acetone | Solution composition (wt %) | | |
|---|---|---|---|---|---|
| | | | Acetone | Mesityl oxide | Isophorone |
| Ex. 2-2 | Ex. 2-1 | 10. ml/H | 64.9 | 2.9 | 17.0 |
| | | 4.7 | 62.2 | 2.7 | 17.8 |
| | | 41.7 | 82.0 | 3.3 | 8.9 |
| Ex. 3-2 | Ex. 3-1 | 5. | 66.3 | 3.1 | 14.2 |
| | | 43 | 86.1 | 3.2 | 5.5 |
| Comp. 2-2 | Comp. 2-1 | 10 | 87.2 | 3.8 | 4.2 |
| | | 40 | 96.7 | 1.4 | 1.0 |

EXAMPLE 4

Example 1-2 was repeated except that cyclohexanone was used in place of the acetone. Cyclohexanone (10 ml/H) was charged and, after two hours, the solution was sampled and assayed by gas chromatography. The results were

| | |
|---|---|
| 2-cyclohexylidenecyclohexanone | 3.7% |
| 2-(1-cyclohexenyl)cyclohexanone | 0.7% |
| cyclohexanone | 94.8% |

We claim:
1. A process for producing aldol condensation dehydration products by condensation dehydration of a carbonyl compound comprising the steps of:
   conducting the aldol condensation dehydration of the carbonyl compound in the pressence of a magnesium aluminum complex compound prepared by allowing a solution of magnesium salts and a solution of aluminum salts to react with ammonia to form a precipitate and heating the precipitate at a temperature within the range of 400° to 700° C. to thereby form the magnesium aluminum complex compound.
2. A process according to claim 1 wherein the magnesium salts are magnesium nitrate or magnesium acetate.
3. A process according to claim 1 wherein the aluminium salts are aluminium nitrate or aluminium lactate.
4. A process according to claim 1 wherein atomic ratio of the magnesium salts to the aluminium salts is 10:1 to 1:5.
5. A process according to claim 1 wherein ammonia is in an amount of 0.5-2 times as much as theoretical equivalents of the magnesium salts and aluminium salts.
6. A process according to claim 1 wherein the carbonyl compounds are acetone.
7. A process for producing an aldol condensation dehydration product comprising the steps of:
   conducting the condensation dehydration of at least one carbonyl compound selected from the group consisting of ketones and aldehydes in the presence of an magnesium.aluminum complex compound obtained by allowing a solution of magnesium salts and a solution of aluminum salts to react with ammonia whereby a precipitate is obtained, the atomic ratio of said magnesium salts to said aluminum salts is 10:1 to 1:5, the amount of ammonia is 0.5-2 times as much as the theoretical equivalence of said magnesium salts and said aluminum salts, and heating said precipitate at a temperature within the range of 400° to 700° C. whereby said magnesium-aluminum complex compound is obtained.

8. The process according to claim 7, wherein the carbonyl compound is selected from the group consisting of acetone, methyl ethyl ketone, methyl isobutyl ketone, diethyl ketone, cyclopentanone and cyclohexanone.

9. The process according to claim 7, wherein the carbonyl compound is selected from the group consisting of acetaldehyde and butyl aldehyde.

10. The process according to claim 7, wherein the condensation dehydration is run under a pressure range of about atmospheric pressure to 5 kg/cm$^2$ and a temperature range of about 250° to 400° C.

11. The process according to claim 7, wherein a feeding speed of the carbonyl compound to the magnesium aluminum complex compounds is about 0.1 to 10 h$^{-1}$ in liquid hourly space velocity.

12. The process according to claim 7, wherein the aldol condensation dehydration products are selected from the group consisting of mesityl oxide and isophorone.

* * * * *